United States Patent [19]

Dejaifve et al.

[11] Patent Number: 4,749,674

[45] Date of Patent: Jun. 7, 1988

[54] CATALYST FOR THE NON-OXIDATIVE DEHYDROGENATION OF ALKYLBENZENE TO ALKENYLBENZENE

[75] Inventors: Pierre E. Dejaifve; Jean-Paul Darnanville; Roland A. C. Garin, all of Grand-Couronne, France

[73] Assignee: Shell Oil Company, Houston, Tex.

[21] Appl. No.: 928,757

[22] Filed: Nov. 10, 1986

[30] Foreign Application Priority Data

Dec. 27, 1985 [FR] France .............................. 85 19324

[51] Int. Cl.$^4$ .......................... B01J 23/10; B01J 23/78
[52] U.S. Cl. ..................... 502/304; 502/302; 585/444

[58] Field of Search .............. 502/302, 304, 303; 585/444

[56] References Cited

U.S. PATENT DOCUMENTS 4,460,706 7/1984 Imanari et al. .................... 502/304
4,467,046 8/1984 Smith et al. ..................... 502/304 X Primary Examiner—W. J. Shine

[57] ABSTRACT

Alkenylbenzenes, e.g. styrene, are prepared by non-oxidative dehydrogenation of alkylbenzenes at elevated temperature in the presence of steam and a novel catalyst comprising iron oxide and, as promoters, an alkali metal compound, ≦10% wt of a compound of a rare earth metal and a calcium compound (not a hydraulic cement) and <1.4% wt of a molybdenum compound.

6 Claims, No Drawings

CATALYST FOR THE NON-OXIDATIVE DEHYDROGENATION OF ALKYLBENZENE TO ALKENYLBENZENE

FIELD OF THE INVENTION

The invention relates to a process for the preparation of an alkenylbenzene by non-oxidative dehydrogenation of an alkylbenzene.

The invention also relates to novel catalysts which may be used for the preparation of alkenylbenzenes, and to a process for the preparation of such catalysts.

BACKGROUND OF THE INVENTION

It is generally known that a commercially important alkenylbenzene, namely styrene, is prepared by dehydrogenation of ethylbenzene in the presence of a catalyst based on iron oxide.

U.S. Pat. No. 4,467,046, issued Aug. 21, 1984, describes a dehydrogenation catalyst containing 15% to 30% $K_2O$, 2% to 8% $CeO_2$, 1.5% to 6% $MoO_3$, 1% to 4% $CaCO_3$, the balance being $Fe_2O_3$. The very high $K_2O$ content and the presence of not less than four metal promoters are disadvantages of this known catalyst.

U.S. Pat. No. 4,460,706, issued July 17, 1984 describes a dehydrogenation catalyst containing 1.5% to 40% by weight of $K_2O$, 11 to 50% by weight of $Ce_2O_3$ (which is equivalent to 11.5% to 52.4% by weight of $CeO_2$), 40% to 87.5% by weight of $Fe_2O_3$ and not over 25% by weight of calcium. The very high cerium content is a disadvantage of this known catalyst.

British Patent Specification No. 1,460,762, published Jan. 6, 1977, describes a dehydrogenation catalyst containing 1 to 40% by weight of an alkali metal compound, 0.5 to 10% by weight of cerium oxide, 5 to 30% by weight of a hydraulic cement as a binding agent, the balance being iron oxide. As hydraulic cement Portland cement may be used.

U.S. Pat. No. 3,223,743, issued Dec. 14, 1965, describes the use of two catalyst layers, one of which contains K or Ca and also Ce.

Japanese Patent Application Publication No. 59,216,634 published Dec. 6, 1984, discloses the use of dehydrogenation catalysts containing a) Mg and Ca and b) Ce and Mo.

German Patent No. DE 3,442,636 Al, published May 22, 1986 describes a dehydrogenation catalyst prepared by kneading a water-containing mixture of (a) 40–90 % wt $Fe_2O_3$; (b) 5–40 % wt $K_2O$; (c) 3–30 % wt MgO; (d) 0–10 % wt $Cr_2O_3$ or $Mn_2O_3$; (e) 0–10 % wt Ce, Mo or W oxide and (f) 0–15 % wt CaO.

It has now been found that a dehydrogenation catalyst containing only three promoters and a limited amount of a cerium compound and which does not need to contain molybdenum is extremely stable.

SUMMARY OF THE INVENTION

The invention provides a process for the preparation of an alkenylbenzene by non-oxidative dehydrogenation of an alkylbenzene, in which process a mixture comprising an alkylbenzene and superheated steam is contacted at elevated temperature with a catalyst comprising iron oxide and, as promoters, an alkali metal compound, not more than 10% by weight of a compound of a rare earth metal, calculated as $MO_2$ on the total catalyst, M representing the rare earth metal, and a calcium compound, with the provisos that the calcium compound is not a hydraulic cement and that the catalyst contains less than 1.4% by weight of a molybdenum compound, calculated as $MoO_3$ on the total catalyst, if any molybdenum compound is present.

DESCRIPTION OF THE PREFERRED EMBODIMENTS

The selectivity to a certain compound, expressed in a percentage, is defined herein as $$\frac{a}{b} \times 100$$

wherein "a" is the amount of alkylbenzene that has been converted into that certain compound and "b" is the total amount of alkylbenzene that has been converted.

The alkali metal compounds which may be used in the process according to the present invention are those of lithium, sodium, potassium, rubidium and cesium. Very good results have been obtained with potassium compounds. The alkali metal compounds are preferably present in the catalyst in an amount of more than 1% by weight, calvculated as alkali metal oxide. Suitable alkali metal compounds are the oxides, hydroxides and carbonates. Catalysts containing more than 25% by weight of an alkali metal compound have as a disadvantage that their bulk crushing strength is not very high.

The rare earth metals which may be used are lanthanum, cerium, praeseodymium, neodymium, promethium, samarium, eurobium, gadolinium, terbium, dysprosium, holmium, erbium, thulium, ytterbium and lutetium. Mixtures of rare earth metals may be used. Very good results have been obtained with cerium compounds. The rare earth metal compounds are preferably present in the catalyst in an amount of more than 1% by weight, calculated as $MO_2$ on the total catalyst, M representing the rare earth metal.

It has been found that the presence of a calcium compound provides the extremely high stability of the catalyst being used in the process according to the present invention. The calcium compound is preferably present in an amount in the range of from 0.1 to 10% and more preferably 0.5 to 5% by weight, calculated as CaO on the total catalyst.

An attractive feature of the process according to the present invention is that the catalyst does not need to contain molybdenum, but, if desired, molybdenum may be present in an amount below 1.4% by weight, calculated as $MoO_3$ on the total catalyst, that is, the molybdenum content will range from 0 to 1.4% by weight.

The process is suitably carried out using a molar ratio steam to alkylbenzene in the range of from 2 to 20 and preferably of from 5 to 13. Another atractive feature of the present process is that relatively low molar ratios steam to alkylbenzene can be used.

The process is suitably carried out at a temperature in the range of from 500° C. to 700° C. An attractive feature of the process is that relatively low temperatures can be used, particularly in the range of from 550° C. to 625° C.

The process may be carried out at atmospheric or super- or subatmospheric pressure. Atmospheric pressure and pressures between 1 bar and 0.5 bar absolute are usually very suitable.

The process is suitably carried out using a liquid hourly space velocity in the range of from 0.1 to 5.0 liter of alkylbenzene per liter of catalyst per h, using, for example, a tubular or radial flow reactor.

The alkylbenzene to be used as a starting compound in the process according to the present invention suitably has 2 to 3 carbon atoms in the alkyl group. Very good results have been obtained with ethylbenzene. Isopropylbenzene is another example of a starting compound. If desired, the aromatic nucleus in the alkylbenzene may carry a second substituent, for example a methyl group.

The catalyst may be used in the form of, for example, pellets, tablets, spheres, pills, saddles, trilobes or tetralobes.

The novel catalysts referred to hereinbefore comprise iron oxide and, as promoters, an alkali metal compound, not more than 10% by weight of a rare earth metal compound, calculated as $MO_2$ on the total catalyst, M representing the rare earth metal and a calcium compound, with the provisos that the calcium compound is not a hydraulic cement and the catalyst contains less than 1.4 percent by weight of a molybdenum compound, calculated as $MoO_3$ on the total catalyst, if any molybdenum is present.

The process for the preparation of the novel catalysts, referred to hereinbefore comprises bringing an alkali metal compound, not more than 10% by weight of a rare earth metal compound, calculated as $MO_2$ on the total catalyst, M representing the rare earth metal and a calcium compound onto iron oxide, with the provisos that the calcium compound is not a hydraulic cement and that the catalyst contains less than 1.4% by weight of a molybdenum compound, calculated as $MoO_3$ on the total catalyst, if any molybdenum is present.

The iron oxide to be used for the preparation of the novel catalysts may be, for example, hydrated or not-hydrated $Fe_2O_3$. The iron oxide may be a synthetically produced, powdered red, red-brown, yellow or black pigment. The red or red-brown pigments are highly pure ferric oxide, while the black pigment is the magnetic form, ferrosoferric oxide ($Fe_3O_4$), which is usually found in the catalyst under various reaction conditions. The yellow iron oxides consist of the monohydrated form of ferric oxide. These oxides are prepared by various methods, for example, oxidation of iron compounds, roasting, precipitation, calcination, and the like. A suitable form of iron compound is the mono-hydrated yellow iron oxide used in the preparation of catalysts according to U.S. Pat. No. 3,360,597, issued Dec. 26, 1967, and U.S. Pat. No. 3,364,277 issued Jan. 16, 1968. Particularly suitable are pigment grade red iron oxides of purities exceeding 98% by weight. These red oxides have surface areas ranging from 2 to 50 $m^2/g$. The alkali metal compound, the cerium compound and calcium compound may be brought into the iron oxide in any suitable manner, for example by intimate mixing iron oxide with suitable alkali metal compound, a suitable cerium compound and a suitable calcium compound in the presence of water. The mixture obtained may be dried and then calcined at a temperature in the range of from, for example, 500° C. to 1200° C.

Suitable alkali metal compounds are, for example, carbonates, hydrogen carbonates, nitrates and acetates; suitable cerium compounds are, for example, cerium nitrate, cerium carbonate and cerium acetate; suitable calcium compounds are calcium nitrate, calcium carbonate, calcium acetate and calcium isobutyrate.

Catalysts having a highly porous structure and a low surface area are highly active in catalytic dehydrogenation. Various methods may be employed to form highly porous catalyst. For example, combustible materials, such as sawdust, carbon, wood flour, etc., may be added during catalyst formation, and then burned out after the pellet has been formed. Many of these porosity-promoting aids also assist in facilitating extrusion of pellets, for example, the use of graphite, potassium alginate and aqueous solutions of methyl cellulose.

If desired, the catalyst may be used supported on a carrier, for example, zinc aluminate.

PREPARATION OF CATALYST 1-4

Catalyst 1 was prepared as follows. Unhydrated $Fe_2O_3$ red oxide (750 g), potassium alginate (37.9 g, potassium content 15% by weight), solid $K_2CO_3$ (140 g) and water (267 ml) were thoroughly mixed and the mass obtained was extruded and pelletized to cylindrical particles having a diameter of 3 mm and a height of 5 mm. The cylinders were dried for 1 h at 50° C., 1.5 h at 75° C. and 3 h at 110° C., calcined for 2 h at 800° C. and then allowed to adopt ambient temperature. Catalyst 1 contained 12% by weight of potassium oxide and 88% by weight of $Fe_2O_3$.

Catalysts 2-4 were prepared by thoroughly mixing catalyst 1 (53 g) with an aqueous solution (18 ml) of metal salts. Table I shows which metal salts and which concentrations thereof in the aqueous solutions were used.

TABLE I

| Catalyst | Metal salt | Concentration of salt per liter solution |
|---|---|---|
| 2 | cerium nitrate.$6H_2O$ | 550 |
| 3 | calcium nitrate.$4H_2O$ | 186 |
| 4 | cerium nitrate.$6H_2O$ | 550 |
|   | calcium nitrate.$4H_2O$ | 186 |

The impregnated cylinders were dried for 0.5 h at 60° C., dried for 2 h at 200° C., calcined for 2 h at 800° C. and then allowed to adopt ambient temperature. Catalysts 1-4 were crushed and a sieved portion of the crushed material, having dimensions between 0.25 and 0.42 mm, was tested as described hereinafter. The composition of each catalyst is stated in Table II hereinafter.

COMPARATIVE EXPERIMENTS A-C and EXAMPLE 1

The experiments described below had the following in common.

A mixture of ethylbenzene and steam, heated to a certain temperature, was introduced at the top of an externally heated, vertically positioned, cylindrical reactor having an internal diameter of 1.0 cm and charged with catalyst (10 ml bulk volume). The mixture was conducted at a pressure of 1 bar and using a liquid hourly space velocity for ethylbenzene of 1 liter per liter of catalyst per hour through the catalyst bed. The temperature was adjusted so that the conversion of ethylbenzene was 70%. The reaction product leaving the reactor was analyzed by means of gas-liquid chromatography. From the data obtained, the conversion of ethylbenzene and the selectivity to styrene were calculated.

The catalysts 1-4 were tested in four experiments using the steam to ethylbenzene molar ratios stated in Table II and adjusting the temperature of the catalyst bed until the conversion of the ethylbenzene was 70%; this temperature is indicated as "T 70". The selectivities to styrene at 70% conversion are indicated as "S 70".

A comparison of the four experiments carried out at a molar ratio steam to ethylbenzene of 12 shows the realtively low temperature and very high selectivity to styrene obtained in Example 1.

The stability of the catalysts was determined at a molar ratio steam to ethylbenzene of 8.5 by determining the average increase of the temperture which was necessary to keep the conversion of ethylbenzene at the constant value shown in Table II for each experiment. This average increase of temperature is indicated in Table II as "°C./day". Table II show that by far the highest stability has been found in Example 1.

C. but at 600° C. Catalyst 6 was tested in the manner of Example 3. The value of T70 was 603° C. and that of S70 was 93.3%.

EXAMPLE 7

Example 6 was repeated under the following conditions:

Liquid hourly space velocity: 0.65 l per l per h.
pressure: 1 bar
temperature: 575° C.
molar ratio steam to ethylbenzene: 8.5.

The conversion of ethylbenzene was constant over a period of 9 days.

COMPARATIVE EXPERIMENT D

TABLE II

| Comparative Experiment | Example | Catalyst No. | Composition, % wt K$_2$O | CeO$_2$ | CaO | Molar ratio steam/ ethylbenzene 12 T70 °C. | S70 % | T °C. | Molar ratio steam/ ethylbenzene 8.5 Conversion % | °C./ day | days on stream |
|---|---|---|---|---|---|---|---|---|---|---|---|
| A | | 1 | 12.0 | — | — | 596.6 | 92.5 | 575 | 50.6 | 2.3 | 4 |
| B | | 2 | 11.2 | 6.9 | — | 602.4 | 92.3 | — | — | unstable | — |
| C | | 3 | 11.8 | — | 1.5 | 609.4 | 93.3 | — | — | not determined | — |
| | 1 | 4 | 11.0 | 6.8 | 1.4 | 602.5 | 93.7 | 575 | 47.7 | 0.2 | 9 |

EXAMPLE 2

Catalyst 5 was prepared as follows. An intimate mixture was prepared stating from unhydrated Fe$_2$O$_3$ (450 g), K$_2$CO$_3$ (84 g), cerium carbonate (Ce$_2$(CO$_3$)$_3$.5H$_2$O, 59,5 g), CaCO$_3$ (13.7 g) and potassium alginate (22.7 g) with gradual addition of water (163 ml) during mixing. The mixture obtained was extruded and pelletized to cylindrical particles having a diameter of 3 mm and a height of 5 mm. The cylinders were dried for 2 h at 75° C. and 3 h at 110° C. and then calcined for 2 h at 800° C. Catalyst 5 contained 80.8% Fe$_2$O$_3$, 11% K$_2$O, 6.8% CeO$_2$ and 1.4% CaO.

Catalyst 5 was tested in the form of the cylinders in the same manner as in Example 1, but using a cylindrical bed having a diameter of 2.7 cm and a height of 17 cm, a temperature of 600° C., a molar ratio of steam to ethylbenzene of 8, a liquid hourly space velocity of 0.65 l per l per h. and a total pressure of 0.76 bar. The value of °C./day was below 0.1° C., measured over 7 days.

EXAMPLE 3

Catalyst 5 was tested in the manner of Example 2, using a molar ratio steam to ethylbenzene of 12, and a pressure of 1 bar. The value of T70 was 606° C. and that of S70 was 92.7%.

EXAMPLE 4

Example 3 was repeated except that the molar ratio steam to ethylbenzene was 8.5, the temperature was 575° C. and the pressure 0.76 bar. The value for °C./day was below 0.3 °C./day, measured over 9 days.

EXAMPLE 5

Example 3 was repeated except that the molar ratio steam to ethylbenzene was 10 and the pressure 0.76 bar. The value of T70 was 602.5° C. and that of S70 was 94.8%.

EXAMPLE 6

Catalyst 6 was prepared in the same manner as catalyst 5 except that the cylinders were not calcined at 800°

Catalyst 7 was prepared in the same manner as catalyst 5 and contained 11% K$_2$O, 17% CeO$_2$, 1.4% CaO, the balance being Fe$_2$O$_3$. Catalyst 7 was tested as in Example 3; the values of T70 and S70 were 606.5° C. and 92.7%, respectively. Comparison with Example 3 shows that increasing the cerium content above 10% by weight does not improve the activity and selectivity of the catalyst.

COMPARATIVE EXPERIMENT E

Catalyst 7 was tested under the same conditions as in Example 7. The temperature had to be increased by 0.3-0.5° C./day over a period 9 days to keep the conversion at a constant value, starting from 575° C. Comparison with Examples 4 and 7 shows that increasing the cerium content above 10% by weight does not improve the stability of the catalyst at low ratios steam to ethylbenzene.

We claim:

1. A catalyst for the non-oxidative dehydrogenation of alkylbenzene to an alkenylbenzene consisting essentially of iron oxide and, as promoters, 1-25 % by weight of an alkali metal compound, calculated as alkali metal oxide on the total catalyst, more than 1 to a maximum of 10 % by weight of a compound of a rare earth metal, calculated as MO$_2$ on the total catalyst, M representing the rare earth metal, and 0.1-10% by weight of a calcium compound, calculated as CaO on the total catalyst with the proviso that the calcium compound is not a hydraulic cement.

2. The catalyst as claimed in claim 1, in which the rare earth metal is cerium.

3. The catalyst as claimed in claim 1, in which the alkali metal compound is a potassium compound.

4. A process for the preparation of a catalyst for the non-oxidative dehydrogenation of an alkylbenzene to an alkenylbenzene in which one or more aqueous mixtures consisting essentially of water, 1-25% by weight of an alkali metal compound, calculated as alkali metal oxide on the total catalyst, more than 1 to a maximum of 10% by weight of a compound of a compound of rare earth metal, calculated as $MO_2$ on the total catalyst, M representing the rare earth metal and/or 0.1–10% by weight of a calcium compound, other than a hydraulic cement, calculated as CaO on the total catalyst is contacted with intimate mixing with iron oxide followed after contact with drying and calcining at tempertures ranging from 500° C. to 1200° C.

5. The process of claim 1 in which the rare earth metal is cerium.

6. The process of claim 1 in which the alkali metal is potassium.

* * * * *